United States Patent
Kikuchi et al.

(10) Patent No.: US 6,435,005 B1
(45) Date of Patent: Aug. 20, 2002

(54) HEATER PATTERNS FOR PLANAR GAS SENSORS

(75) Inventors: Paul C. Kikuchi, Fenton; Lone-Wen F. Tai, Rochester Hills; Walter T. Symons, Grand Blanc, all of MI (US)

(73) Assignee: Delphi Technologies, Inc., Troy, MI (US)

( * ) Notice: Subject to any disclaimer, the term of this patent is extended or adjusted under 35 U.S.C. 154(b) by 0 days.

(21) Appl. No.: 09/741,597

(22) Filed: Dec. 19, 2000

(51) Int. Cl.[7] .......................... G01N 27/12; G01N 7/00; G01N 27/00; H01L 7/00
(52) U.S. Cl. .................. 73/25.01; 73/23.32; 73/31.05; 338/34; 422/94; 29/595; 29/611
(58) Field of Search .............................. 73/25.01, 31.05, 73/23.2, 23.32, 23.31; 422/88, 94, 95; 338/34; 29/25.01, 595, 611, 825

(56) References Cited

U.S. PATENT DOCUMENTS

| | | | |
|---|---|---|---|
| 4,146,957 A | | 4/1979 | Toenshoff ..................... 29/612 |
| 4,241,019 A | * | 12/1980 | Nakatani et al. ............... 422/94 |
| 4,413,502 A | * | 11/1983 | Ohta et al. ...................... 73/23 |
| 4,453,397 A | * | 6/1984 | Ohta et al. ...................... 73/23 |
| 4,520,653 A | * | 6/1985 | Kaiser ............................ 73/23 |
| 4,697,165 A | * | 9/1987 | Ishiguro et al. ............... 338/34 |
| 4,952,903 A | * | 8/1990 | Shibata et al. ................ 338/34 |
| 5,017,340 A | * | 5/1991 | Pribat et al. ................... 422/98 |
| 5,038,609 A | | 8/1991 | Kumada ................... 73/204.24 |
| 5,288,389 A | | 2/1994 | Yamada et al. .............. 204/425 |
| 5,342,498 A | | 8/1994 | Graves et al., Jr. ......... 204/408 |
| 5,544,640 A | * | 8/1996 | Thomas et al. ............. 123/689 |
| 5,777,207 A | * | 7/1998 | Yun et al. ................... 73/31.05 |
| 5,804,050 A | * | 9/1998 | Hayakawa et al. ......... 204/424 |
| 5,804,699 A | * | 9/1998 | Sugiyama et al. .......... 73/23.32 |
| 5,895,591 A | | 4/1999 | Kojima et al. ............... 219/209 |
| 6,145,371 A | * | 11/2000 | Watson ...................... 73/31.06 |
| 6,161,421 A | * | 12/2000 | Fang et al. ................. 73/31.05 |

FOREIGN PATENT DOCUMENTS

| | | |
|---|---|---|
| EP | 0963829 | 12/1999 |
| JP | 60142241 | 7/1985 |
| JP | 5209854 | 8/1993 |

* cited by examiner

*Primary Examiner*—Hezron Williams
*Assistant Examiner*—David J. Wiggins
(74) *Attorney, Agent, or Firm*—Vincent A. Cichosz

(57) ABSTRACT

A heater pattern for a heater of a gas sensor in which a temperature profile is manipulated utilizes a thermistor element arranged in an electrically serial configuration and disposed on a substrate. The thermistor element is arranged so as to define an edge pattern extending about a perimeter of the substrate and a center pattern serially connected to the edge pattern. The center pattern extends over a portion of the substrate that is intermediate the perimeter of the substrate. In a preferred embodiment, the thermistor element is screen printed onto the substrate to a thickness of about 5 microns to about 50 microns, and preferably to a thickness of about 10 microns to about 40 microns. The edge and center patterns are furthermore preferably formed of materials having differing coefficients of thermal resistivity, e.g., platinum and platinum/palladium blends. A method of heating the gas sensor includes disposing the thermistor element in an electrically serial configuration about a perimeter of the substrate and over a portion of the substrate intermediate the perimeter of the substrate and pass an electric current through the thermistor element.

11 Claims, 2 Drawing Sheets

HEATER PATTERNS FOR PLANAR GAS SENSORS

TECHNICAL FIELD

This disclosure relates to planar gas sensors, and, more particularly, to heater patterns for planar gas sensors that yield a reduction in the incidence of cracking attributable to tensile stresses at the edges of the planar gas sensors.

BACKGROUND

Gas sensors, and in particular oxygen sensors are used in combustion engines to control the air/fuel ratio in the combustion chamber so that the air/fuel ratio remains at or near its proper stoichiometric value. Maintaining the proper stoichiometric value, allows for the improvement of fuel consumption and the minimization of pollutants in an exhaust gas. An oxygen sensor typically includes an oxygen sensing element having an ion-conductive solid electrolytic plate on which porous electrodes are disposed. A difference in potential corresponding to the difference in oxygen content between the exhaust gas and the reference air is generated by the oxygen sensing element, is quantified, and is used to adjust the air/fuel ratio in the combustion chamber.

The proper functioning of the oxygen sensing element is typically dependent upon its temperature. Because a significant amount of time is often required for the oxygen sensor to become heated to operating temperature after startup of the engine, the air/fuel ratio is difficult to control during that time. Heaters are, therefore, oftentimes incorporated into the oxygen sensing system to more quickly bring the oxygen sensing elements up to a temperature at which the most efficiency can be realized.

Typical heaters in planar sensors are formed in various patterns on one face of the oxygen sensing element. Such designs attempt to create a uniform temperature profile across the sensor element by adjusting the heat input through patterning of a single heater trace. Heater patterns such as these are difficult to control because the balance of the heat input between the center and the edges of the pattern changes as the temperature changes. Variations in the heating profile oftentimes cause "hotspots" within the oxygen sensing element, which result in thermal shock. In such a configuration, because the oxygen sensing element is usually fabricated from a ceramic material, differing rates of expansion often cause tensile stresses to be experienced along the interfaces of the hotter and colder areas. Such tensile stresses may, over time, cause the oxygen sensing elements to fracture and function improperly, thereby communicating inaccurate information for the control of the air/fuel ratio. In such an instance, the oxygen sensor will require replacement to ensure maximum efficiency of the system operation.

BRIEF SUMMARY

A heater pattern for a heater of a gas sensor in which a temperature profile is manipulated is described below. The heater pattern utilizes a thermistor element configured in such a manner so as to reduce the number of hotspots in the gas sensor. The heater includes a substrate and the thermistor element disposed thereon. The thermistor element is arranged so as to define an edge pattern extending about a perimeter of the substrate and a center pattern serially connected to the edge pattern. The center pattern extends over a portion of the substrate that is intermediate the perimeter of the substrate. In a preferred embodiment, the thermistor element is screen printed onto the substrate to a thickness of about 5 microns to about 50 microns, and preferably to a thickness of about 10 microns to about 40 microns. The edge and center patterns are furthermore preferably formed of materials having differing coefficients of thermal resistivity, e.g., platinum and platinum/palladium blends. A method of heating the gas sensor includes disposing the thermistor element in an electrically serial configuration about a perimeter of the substrate and over a portion of the substrate intermediate the perimeter of the substrate and pass an electric current through the thermistor element.

The above-described and other features and advantages of the present invention will be appreciated and understood by those skilled in the art from the following detailed description, drawings, and appended claims.

BRIEF DESCRIPTION OF THE DRAWINGS

The apparatus and method will now be described by way of example, with reference to the accompanying drawings, which are meant to be exemplary, not limiting.

DETAILED DESCRIPTION

A heater pattern for a heater of a planar gas sensor is described herein. Although an oxygen sensor is described, the gas sensor could be a nitrogen sensor, a hydrogen sensor, a hydrocarbon sensor, or a similar apparatus. Unlike heater patterns of the prior art, which typically include a single thermistor element extending about an outer edge of the heater, the disclosed heater pattern utilizes a thermistor element that extends about the outer edge of the heater as well as over the portion of the heater intermediate the outer edge. In such a design, the temperature differential between the edges of the heater and the center portion of the heater is minimized, thereby causing the heat transfer between the outer edge and the center portion of the heater to be minimized. Because less heat is transferred across the surface of the substrate upon which the heater is disposed, tensile stresses at the edges of the heater are reduced. Although the following description is drawn to a heater pattern for a planar oxygen sensor, it should be understood that the sensor into which the heater pattern could be incorporated could be a conical sensor.

Figure 1:
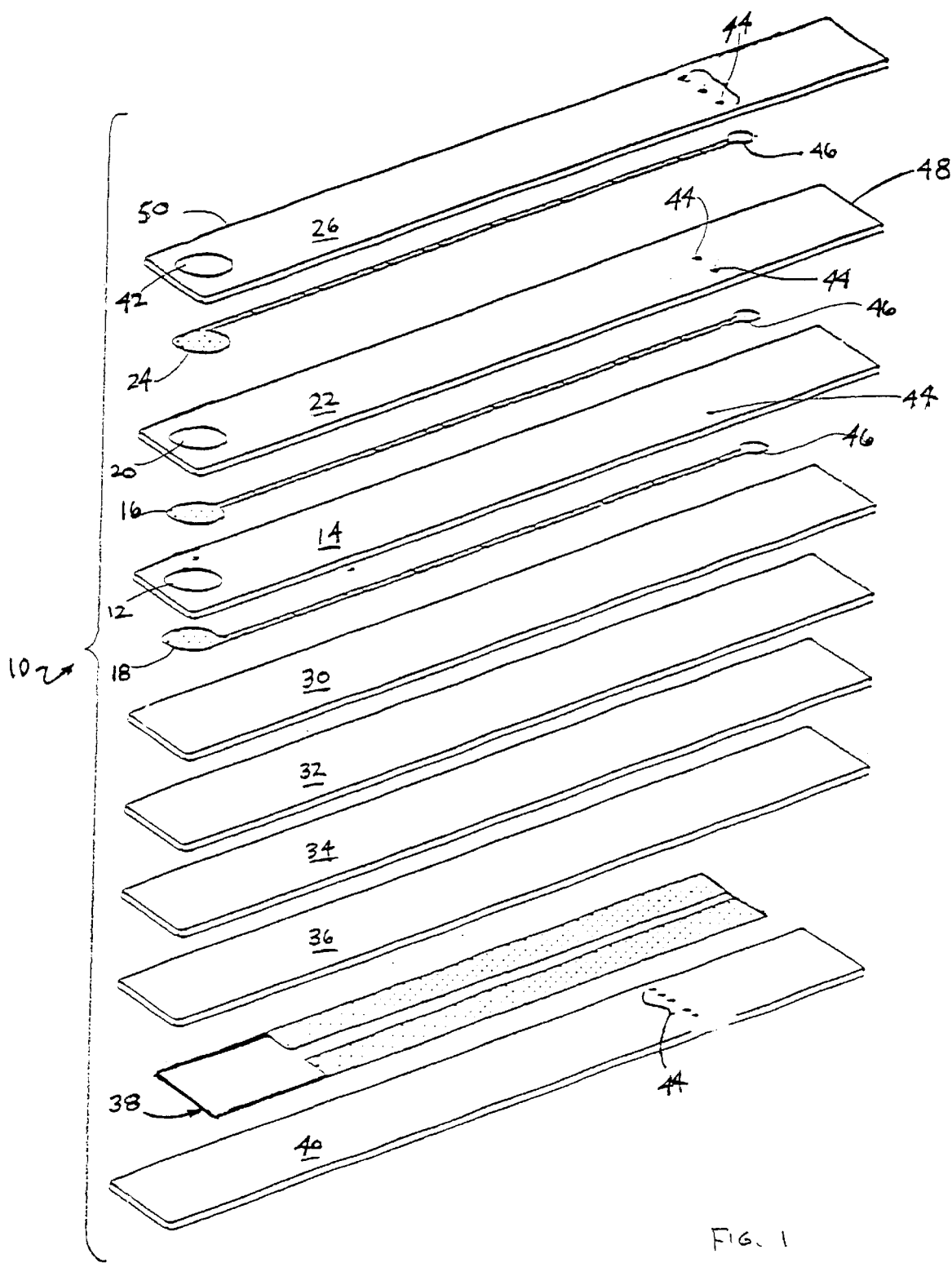
FIG. 1 is an exploded view of an embodiment of a planar oxygen sensor element.

Referring to FIG. 1, a typical arrangement of the different layers of a sensor element, shown generally at 10, is illustrated. Sensor element 10 comprises a solid electrolyte 12 disposed in a dielectric layer 14 with an inner electrode 16 and a reference electrode 18 disposed on opposite sides of solid electrolyte 12; a porous electrolyte 20 disposed in electrical communication with inner electrode 16 and disposed in a dielectric layer 22; an outer electrode 24 disposed on the side of porous electrolyte 20 opposite inner electrode 16; and a dielectric layer 26 disposed against dielectric layer 22 opposite dielectric layer 14. Sensor element 10 further comprises internal support layers 30, 32, 34, 36 disposed against dielectric layer 14; a heater, shown generally at 38, disposed between support layer 36 and a protective outer layer 40; a protective material 42 disposed in fluid communication with outer electrode 24 and within dielectric layer 26; vias 44 formed in dielectric layers 14, 22, 26, and outer layer 40; leads 46 in electrical communication with electrodes 16, 18, 24. A terminal end of sensor element 10 is shown generally at 48, and a sensor end of sensor element 10 is shown generally at 50. A heater pattern (not shown) is disposed on heater 38 and is described below with reference to FIG. 2.

Outer electrode 24, porous electrolyte 20, and inner electrode 16 form a pumping cell, while inner electrode 16, solid electrolyte 12, and reference electrode 18 form a reference cell. Oxygen in the exhaust gas enters the pumping cell through protective material 42 and diffuses through outer electrode 24 and porous electrolyte 20 to inner electrode 16, where the oxygen is ionized and pumped back out of the cell. Generally, a reference cell is used in combination with the pumping cell, but the pumping cell can be used as the only electrochemical cell in the sensor in lean-only applications. The reference cell is used to compare the partial pressure of oxygen at inner electrode 16 with a known oxygen partial pressure at reference electrode 18 in order to determine the potential that should be applied to the pumping cell. The measured current in the pumping cell will be proportional to the partial pressure of oxygen in the exhaust gas.

Leads 46 are disposed across dielectric layers 14, 22 to electrically connect the external wiring of sensor element 10 with electrodes 16, 18, 24. Leads 46 are typically formed on the same layer as the electrode to which they are in electrical communication and extend from the electrode to the terminal end 48 of the element where they are in electrical communication with the corresponding via 44. Heater 38 also includes leads (shown below with reference to FIG. 2) that are in electrical communication with vias 44.

Figure 2:
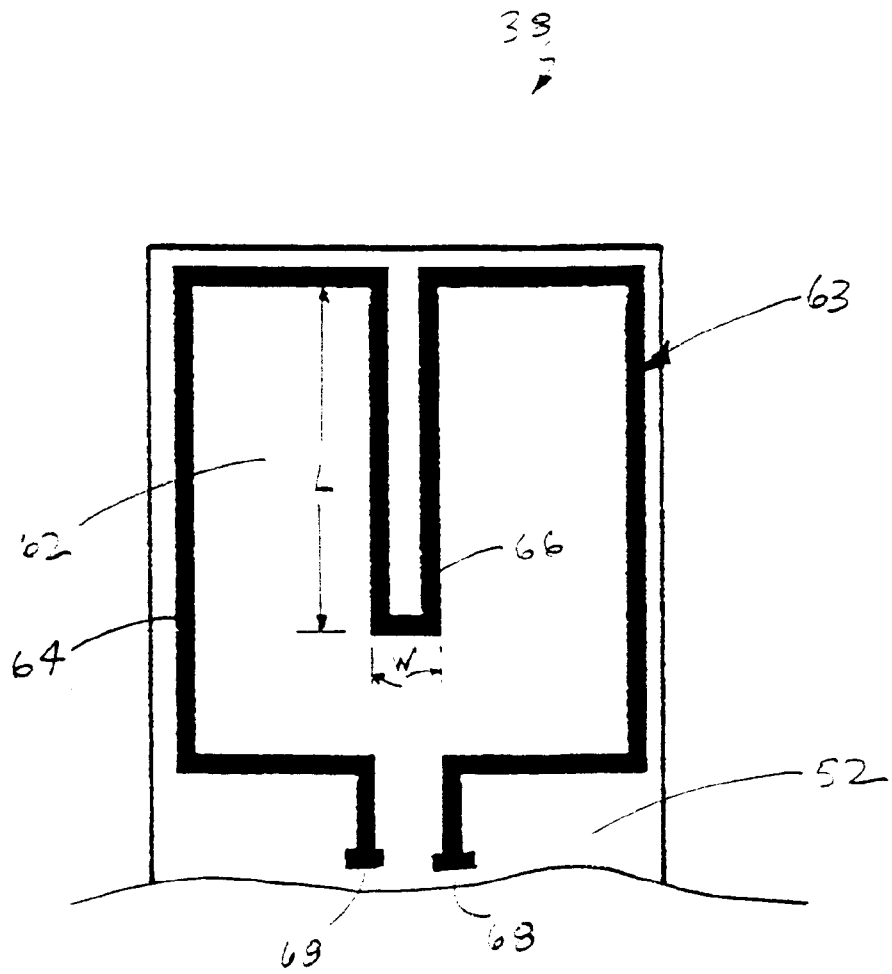
FIG. 2 is a plan view of an embodiment of a heater pattern disposed on a substrate.

Referring now to FIG. 2, heater 38 is shown in greater detail. Heater 38 comprises a thermistor element, shown generally at 63, configured to define a heating section 62 and leads 68 disposed on a substrate 52 and positioned between the adjacent layers of the sensor element. Preferred materials for use as substrate 52 include, but are not limited to, alumina, alumina-based compounds, ceramics, glasses, cermets, and combinations of at least one of the foregoing materials.

Heating section 62 comprises an edge pattern 64 and a center pattern 66 arranged in an electrically serial configuration. Edge pattern 64 extends generally about an outer edge of heating section 62 that corresponds with a perimeter of substrate 52. Center pattern 66 extends from edge pattern 64 substantially over a portion of heating section 62 intermediate the perimeter of substrate 52. Center pattern 66 is preferably arranged on substrate 52 substantially in the form of a U shape, the ends of the legs of the U shape each being in electronic communication with edge pattern 64. Such an arrangement maximizes the area of substrate 52 over which center pattern 66 is disposed. By maximizing the area over which center pattern 66 is disposed, the number of temperature differentials created within heating section 62 is minimized and heater 38 is provided with improved heating capabilities.

The proper flow of current to heating section 62, which is selected in the design of heater 38, raises the temperature of the sensor element such that the air/fuel ratio can be adequately controlled immediately after startup of an engine (not shown) into which the sensor element incorporating heater 38 is installed and before the engine reaches its operating temperature. Because thermistor element 63 is resistive, the application of a current therethrough causes heat to be generated. The flow of current is effectuated through heater leads 68, which are disposed on the end portions of edge pattern 64 of thermistor element 63 and are connectable to a power source (not shown) that provides a flow of current to heating section 62.

Thermistor element 63 typically comprises a precious metal that may be deposited onto substrate 52 in a myriad of ways including, but not limited to, sputtering, chemical vapor deposition, stenciling, and screen printing. Thicker depositions of material are generally screen printed or stenciled onto substrate 52, while thinner depositions of material are generally sputtered or deposited using vapor deposition techniques. In a preferred embodiment, the metal is formed into a paste, screen printed onto substrate 52, and dried. The metal is typically combined with cellulose, a binder, and a solvent to make the paste. Once the paste is applied to the substrate, dried, and sintered onto the substrate, each pattern 64, 66 is about 5 microns to about 50 microns thick. A preferred thickness for each pattern 64, 66 is about 10 to about 40 microns.

Variations in the dimensions of center pattern 66 allow the heating characteristics of thermistor element 63 to be adjustable. These variations are effectuated by the alteration of a length L of center pattern 66. By altering length L of center pattern 66, increased contact between substrate 52 and thermistor element 63 can be maintained. Such increased contact minimizes the presence of hotspots in heater 38 and provides a more uniform temperature profile over the surface of substrate 52. A width W of center pattern 66 is also variable and can be manipulated to give additional flexibility in adjusting the heat input to center pattern 66.

In an additional embodiment of thermistor element 63, patterns 64, 66 may be fabricated of materials having varying thermal coefficient of resistivity (TCR) values. The TCR, which is typically measured in parts per million per degree temperature, is characterized by an increase in resistance for each degree increase of temperature over a given range. Materials having a high TCR are typically used for center pattern 66 so that a greater change in resistance per degree temperature can be realized. Because the heat gradient is preferably from the innermost portions of sensor to the outermost portions, materials having a TCR lower than the TCR of center pattern 66 are typically used for edge pattern 64. In such an instance, as the temperature of center pattern 66 increases, the TCR of the material from which center pattern 66 is fabricated causes a higher resistance to be realized by center pattern 66. When this higher resistance is realized, the current through center pattern 66 is reduced, which in turn reduces the heat generated by center pattern 66. When the heat generated is reduced, the disparity in temperatures between center pattern 66 and edge pattern 64 is minimized and a more uniform temperature profile across the surface of heater 38 is attained. Uniformity in the profile across the surface of heater 38 minimizes tensile stresses that result from the differing rates of expansion associated with heating section 62.

The variations in the TCRs of each pattern 64, 66 can be realized through appropriate selection of conductor materials. The preferred material for center pattern 66 includes, but is not limited to, platinum, which has an inherent TCR of about 3928 ppm/° C. The preferred material for edge pattern 64 includes, but is not limited to, a blend of platinum and palladium. The preferred materials for leads 68 include, but are not limited to, nickel, blends of nickel and chromium, and blends of nickel, chromium, and gold.

In the operation of an exhaust sensor incorporating heater 38, the power source supplies battery voltage to patterns 64, 66. The voltage supplied is typically a constant value (for example, about 13.5 volts DC) measured across leads 68. Because patterns 64, 66 are serially configured and because the voltage is substantially constant over the total length of thermistor element 63, the current through each pattern 64, 66 is a function of the resistance of each pattern 64, 66 and is defined by the equation I=E/R. Furthermore, because center pattern 66 is generally fabricated of a material having a higher TCR value than edge pattern 64 has, and because the resistance of center pattern 66 preferably varies to a greater degree than does the resistance of edge pattern 64 due to the materials of construction, a temperature gradient associated with heater 38 typically results in the transfer of heat from the inner portions of substrate 52 to the edge portions of substrate 52. Because of such a transfer of heat, a more uniform temperature profile across heater 38 is realized.

While preferred embodiments have been shown and described, various modifications and substitutions may be made thereto without departing from the spirit and scope of the invention, including the use of the geometries taught herein in other conventional sensors. Accordingly, it is to be understood that the apparatus and method have been described by way of illustration only, and such illustrations and embodiments as have been disclosed herein are not to be construed as limiting to the claims.

What is claimed is:

1. A gas sensor element, comprising:
   an electrochemical cell;
   a substrate disposed within said electrochemical cell; and
   a heater disposed on said substrate and in thermal communication with said electrochemical cell, said heater comprising a thermistor element, said thermistor element comprising an edge pattern extending about a perimeter of said substrate and a center pattern serially connected to said edge pattern and extending over a portion of said substrate intermediate said perimeter of said substrate, wherein said edge pattern and said center pattern are formed of materials having differing thermal coefficients of resistivity.

2. The gas sensor of claim 1 wherein the first material is platinum, and wherein the second material comprises a blend of platinum and palladium.

3. A heater for a gas sensor, comprising:
   a substrate; and
   a thermistor element disposed on said substrate, said thermistor element arranged so as to define an edge pattern extending about a perimeter of said substrate and a center pattern serially connected to said edge pattern and extending over a portion of said substrate intermediate said perimeter of said substrate, wherein said thermistor element is deposited onto said substrate to a thickness of about 10 microns to about 40 microns.

4. A heater for a gas sensor, comprising:
   a substrate; and
   a thermistor element disposed on said substrate, said thermistor element arranged so as to define an edge pattern extending about a perimeter of said substrate and a center pattern serially connected to said edge pattern and extending over a portion of said substrate intermediate said perimeter of said substrate, wherein said edge pattern and said center pattern are formed of materials having differing coefficients of thermal resistivity.

5. The heater of claim 4 wherein said thermistor element is screen printed onto said substrate.

6. The heater of claim 4 wherein said thermistor element is deposited onto said substrate to a thickness of about 5 microns to about 50 microns.

7. The heater of claim 4 wherein said edge pattern comprises a blend of platinum and palladium.

8. The heater of claim 7 wherein said center pattern comprises platinum.

9. A method of heating a planar gas sensor, comprising:
   passing an electric current through a thermistor element comprising an edge pattern extending about a perimeter of said substrate and a center pattern serially connected to said edge pattern and extending over a portion of said substrate intermediate said perimeter of said substrate, wherein said edge pattern and said center pattern are formed of materials having differing thermal coefficients of resistivity.

10. The method of claim 9 wherein said disposing of said thermistor element further comprises selecting materials for said thermistor element such that a portion of said thermistor element disposed about said perimeter of said substrate allows for a lower resistance to be realized therethrough than does a portion of said thermistor element disposed over said portion of said substrate intermediate said perimeter of said substrate.

11. A method for making a gas sensor, comprising:
   forming an electrochemical cell;
   disposing a heater in thermal communication with the electrochemical cell, said heater comprising a thermistor element comprising an edge pattern extending about a perimeter of said substrate and a center pattern serially connected to said edge pattern and extending over a portion of said substrate intermediate said perimeter of said substrate, wherein said edge pattern and said center pattern are formed of materials having differing thermal coefficients of resistivity.

* * * * *